United States Patent [19]

Flores-Valderrama de Gonzalez

[11] Patent Number: 5,782,856
[45] Date of Patent: Jul. 21, 1998

[54] OBSTETRICAL PNEUMOGIRDLE

[76] Inventor: Maria de la Luz Flores-Valderrama de Gonzalez, Andes #2722, Col. Jardin Obispado, 64010 Monterrey, Nuevo Leon, Mexico

[21] Appl. No.: 654,617

[22] Filed: May 29, 1996

[51] Int. Cl.$^6$ ............................................. A61B 17/00
[52] U.S. Cl. ............................ 606/201; 606/202; 128/118.1
[58] Field of Search ............................ 606/201, 202; 128/118.1

[56] References Cited

U.S. PATENT DOCUMENTS

| | | | |
|---|---|---|---|
| 1,982,505 | 11/1934 | Emerson | 606/202 |
| 3,825,008 | 7/1974 | Shook | 606/202 |
| 5,383,894 | 1/1995 | Dye | 606/201 |

FOREIGN PATENT DOCUMENTS 0009265 of 1908 United Kingdom ............... 128/118.1

*Primary Examiner*—Michael Buiz
*Assistant Examiner*—Kevin Truong
*Attorney, Agent, or Firm*—Laurence R. Brown

[57] ABSTRACT

This invention relates to an obsterical pneumogirdle having a body formed by a front section and a back section between which an inflatable chamber is placed. When inflated, the chamber remains located exactly over the front wall of a pregnant woman's abdomen, in such a way that appropriate intermittent pressure may be exerted over the patient's womb. This obstertrical pneumogirdle also comprises a monitor, a manometer a pneumatic electronic control system, an inlet for oxygen or air, a pressure adjustment knob, cables for electric feeding, a hose for pressure monitoring, a plurality of girdle braces, a switch to start or stop the system's operation, an air hose and switch to start or stop air flow is interconnected to an air pump, and devices to fasten the girdle to the patient's body. All these components are disposed in such a way to make the air injection possible as well as the regulation of pressure, and further, to procure a safe, calm and efficient childbirth.

5 Claims, 3 Drawing Sheets

OBSTETRICAL PNEUMOGIRDLE

BACKGROUND OF THE INVENTION

So far, to aid childbirth, forceps, extractors and many other type of mechanisms have been used as common means to try to extract the fetus on the inside of the uterus during childbirth. Said instruments have been used since immemorial time, however, as it is well known by medical science, their use involves some risk for the fetus, because many times it overpasses the tolerable limits and injuries are produced.

SUMMARY OF THE INVENTION

By the use of this invention a delivery work has been achieved in multiple childbirth, more natural and with much less danger for the fetus, because this invention works in concert with the spasms produced by the contractions, helping the muscular activity while exerting additional pressure during expulsion period. This invention works at the same time as each contraction takes place and relaxes after each contraction, so it does not interfere with the appropriate circulation of the uterusplacenta and the convenient oxygenation of the fetus.

DESCRIPTION OF THE PREFERRED EMBODIMENT

Figure 1:
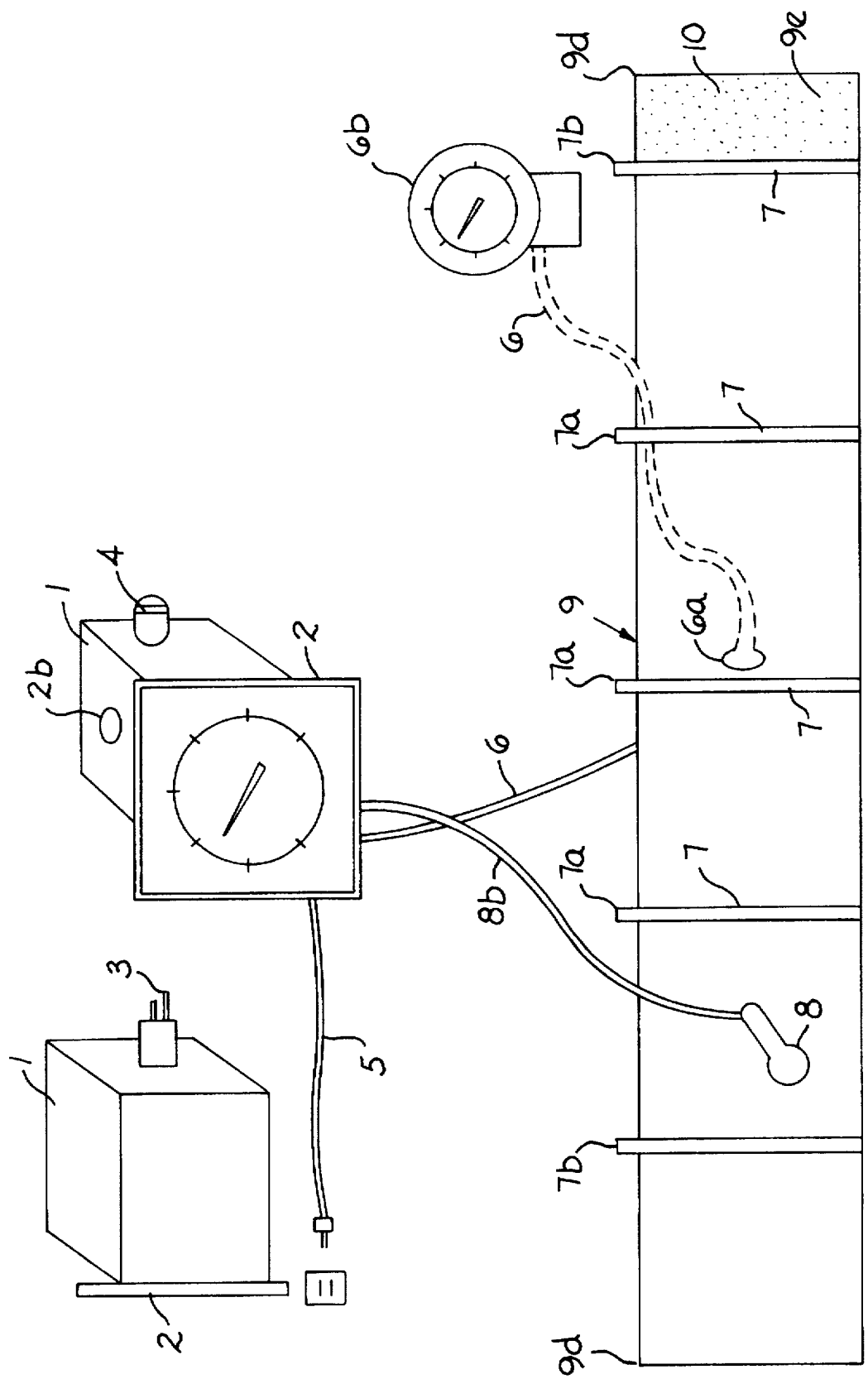
FIG.1 shows a schematic view of the girdle and the different components which compose it.

In reference to said figures, this invention provides a pneumatic electronic control (1), in which a monitor (2B) is located, by means of which it is possible to visualize if the pneumatic electronic control (1) has been turned on. Also, part of the system is a manometer (2) provided with an inlet of oxygen or air (3) by means of which oxygen or air are fed to the pneumatic electronic control system (1).

The system also contains with a pressure adjustment knob (4) to adjust the necessary air pressure in the air chamber (11) in order to provide to the patient the constant or intermittent pressure needed in her case.

With the purpose of energizing the system, the pneumatic electronic control system (1) is provided with an appropriate air pump (of common knowledge), by means of which it is possible to pump air into the chamber (11), through the secondary hose (8B). The pneumatic electronic control system (1) has with an electric feeding cable (5) which provides the electric current necessary for the pneumatic electronic control system (1), said cable being connected to a power source of alternating current, or a power source of direct current (a battery). The obstetric pneumogirdle (9) also contains an emergency inlet (6A) to which at a desired time a secondary hose (6) may be connected, to monitor the pressure through a manual manometer (6B). This would permit the doctor delivering the baby to constantly visualize the pressure exerted over the patient's (13) womb (12).

The obstetric pneumogirdle (9) is formed by a flexible and elongated body, which comprises a front section (9A) and a back section (9B) joined together longitudinally in their sides, producing an interior space (9C) between primary boards or braces (7A). In this interior space (9C) the air chamber (11) will be sheltered. Additionally, along the obstetric pneumogirdle, many secondary braces (7B) are placed in order to provide to the obstetric pneumogirdle (9) firmness of position or the needed rigidity.

In its ends (9D) the obstetric pneumogirdle counts with subjection elements (9E) of common knowledge (Velcro, buckles, fasteners, etc.).

In order to automatically operate the pneumatic electronic control system (1), the system is provided with a switch to start and stop (8) which, by means of the secondary hose (8B), sends the necessary air volume to inflate or deflate the air chamber (11), thus interrupting or working the pneumatic electronic control system (1).

OPERATING METHOD

Figure 2:
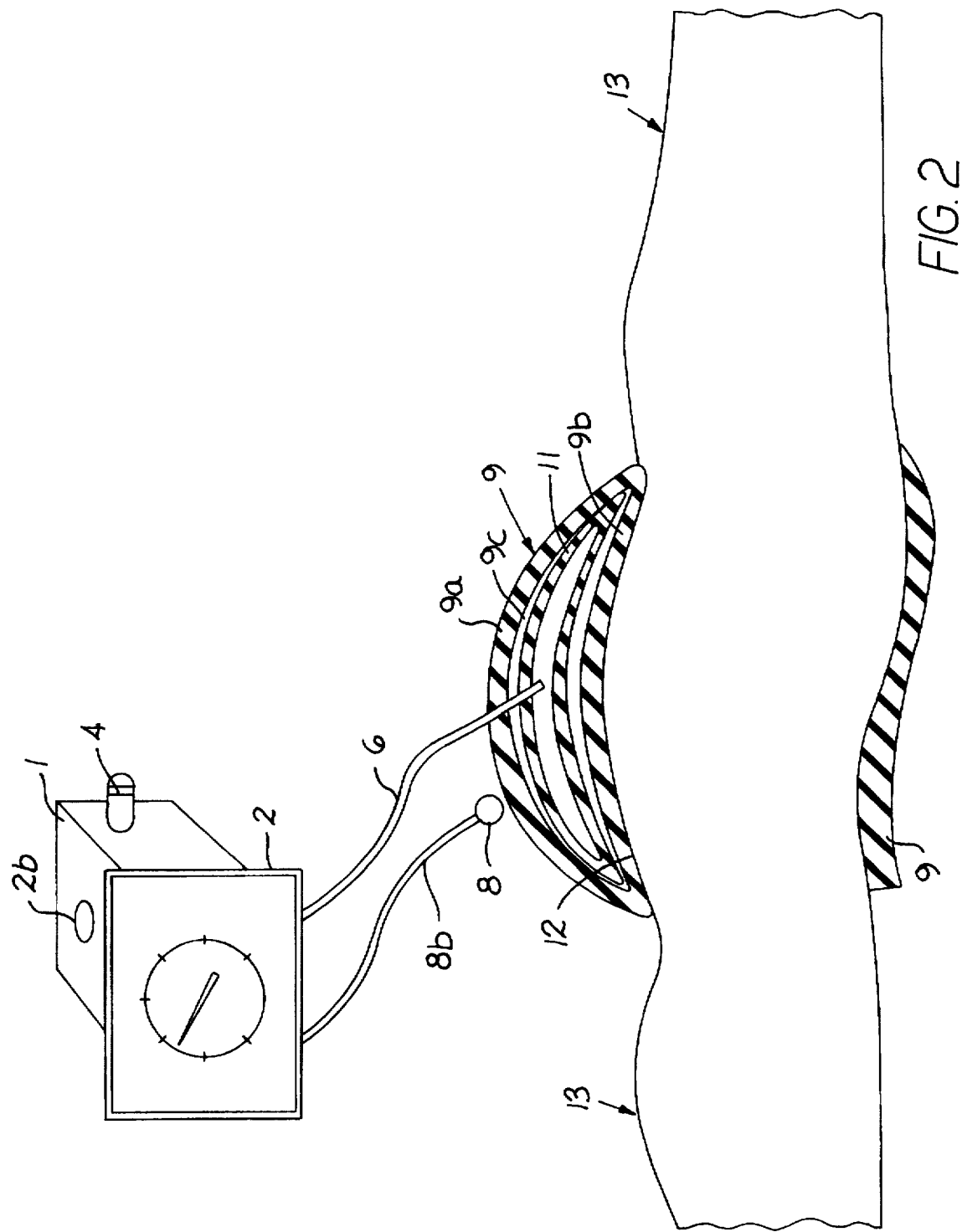
FIG.2 shows a longitudinal view of the patient and the girdle placed over the womb.
Figure 3:
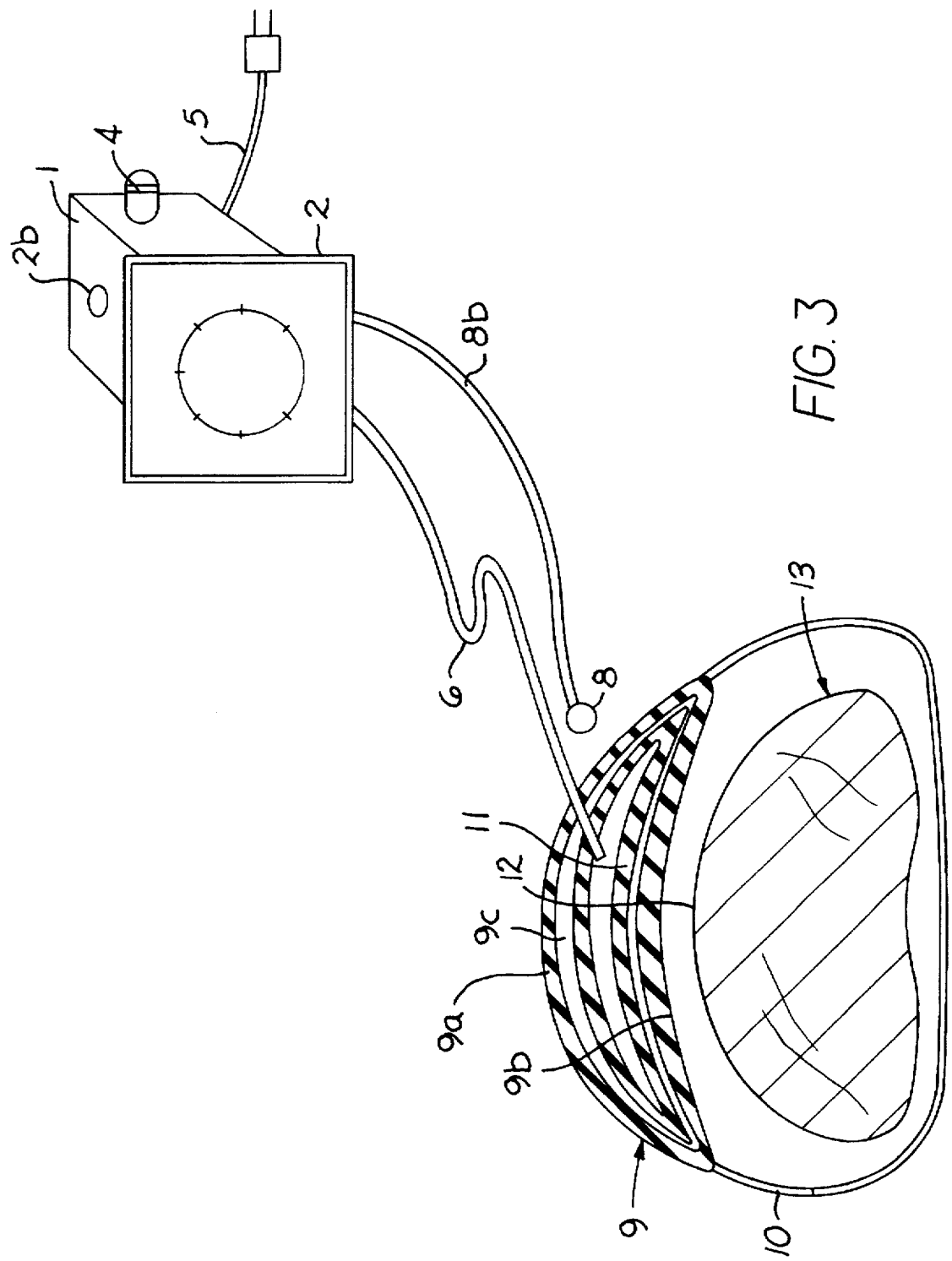
FIG.3 shows a cross sectional view of the patient's body and the girdle placed over her womb.

The operation of the obstetric pneumogirdle (9) begins (FIGS. 2 and 3), placing the same around the patient's (13) womb (12), in such a way that the air chamber (11) stays over the womb (12) of the patient (13) and remains fixed in such position by means of the zippers (10). When this is achieved, the operation of the pneumatic electronic control (1) is initiated by means of the hose (6), which begins to inject air to the air chamber (11) measuring the pressure with the manometer (2) or the secondary manometer (6B). When the desired pressure is obtained, the pneumatic electronic control (1) automatically stops, air can be liberated immediately, and injection can be initiated again in order to give an alternating pressure, as the childbirth requires.

What is claimed is:

1. An obstetric pneumogirdle system for aiding childbirth, comprising in combination:

a girdle for placement over a patient's womb having inflatable internal chamber means for applying intermittent forces to the womb for aiding childbirth, and an electronic control system for use of a childbirth attendant to control pressure being exerted by the girdle on the womb providing an intermittently actuable control for applying additional pressure on the womb during expulsion of a fetus in concert with childbirth spasms produced by contractions and for conversely reducing the pressure exerted on the womb after the contractions, comprising: means to release air from said internal chamber, an electric air pump connected to pump air into said internal chamber, electronic switching means for inserting air into and releasing air from the internal chamber, and pressure control means for adjusting the air pressure monitoring means for measuring during childbirth the air pressure within said chamber.

2. The pneumogirdle system of claim 1 further comprising, an elongated girdle body of a flexible fabric material having front and back sections joined together over said internal chamber and means for securing the girdle body about a maternity patient to place the internal chamber over the womb.

3. The system of claim 2 further comprising a plurality of spaced braces laterally disposed across the girdle body over the region of the womb.

4. The system of claim 2 further comprising means for selectively coupling a pressure monitoring instrument directly to an internal cavity of the girdle.

5. An obstetrical pneumogirdle system comprising in combination a pneumatically inflatable girdle adapted to be placed over a womb during childbirth, including means for intermittently inflating and deflating the girdle to produce additional pressure on the womb in concert with childbirth spasms produced by contractions, a set of controls for use by a childbirth attendant to manually control the pressure applied to the womb during expulsion of the fetus, and pressure monitoring means for monitoring the pressures exerted on the womb during childbirth.

* * * * *